United States Patent [19]

Summers

[11] Patent Number: 5,638,824
[45] Date of Patent: Jun. 17, 1997

[54] ULTRASONIC MONITOR

[75] Inventor: John Brian Summers, 52 Bushy Mill Lane, Watford, Hertfordshire, Great Britain

[73] Assignees: Advanced Monitors Holdings Limited; John Brian Summers, both of Hamshire, Great Britain

[21] Appl. No.: 507,469

[22] PCT Filed: Feb. 21, 1994

[86] PCT No.: PCT/GB94/00343

§ 371 Date: Aug. 24, 1995

§ 102(e) Date: Aug. 24, 1995

[87] PCT Pub. No.: WO94/20021

PCT Pub. Date: Sep. 15, 1994

[30] Foreign Application Priority Data

| Feb. 25, 1993 | [GB] | United Kingdom | 9303861 |
| Oct. 5, 1993 | [GB] | United Kingdom | 9320468 |

[51] Int. Cl.⁶ .................................................. A61B 8/00
[52] U.S. Cl. ............................................................ 128/721
[58] Field of Search ..................... 128/660.01, 661.07, 128/661.08, 661.09, 719, 720, 721; 73/620, 621; 340/552, 554, 573; 342/104, 27, 28

[56] References Cited

U.S. PATENT DOCUMENTS

| 3,942,513 | 3/1976 | Frank | 128/721 |
| 4,107,659 | 8/1978 | Massa | 340/552 |
| 4,399,703 | 8/1983 | Matzuk | 73/621 |
| 4,738,266 | 4/1988 | Thatcher | 128/719 |
| 4,819,652 | 4/1989 | Micco | 128/661.09 |
| 5,455,588 | 10/1995 | Lew et al. | 342/104 |

*Primary Examiner*—George Manuel
*Attorney, Agent, or Firm*—Ronald M. Anderson

[57] ABSTRACT

An ultrasonic monitor is disclosed for monitoring movement, such as breathing of a human or animal, or low frequency vibration of civil engineering structures. The monitor may also be used in measuring fluid properties such as flow rate or viscosity. The monitor operates by periodically emitting bursts of ultrasound pulses from an emitter (1), and subsequently detecting the pulses by a receiver (6), for example after reflection from a target object (13) such as a sleeping baby. Changes in condition are determined by monitoring the changes in phase occurring between the input to the emitter (1) and the output from the receiver (6).

29 Claims, 7 Drawing Sheets

FIG. 4
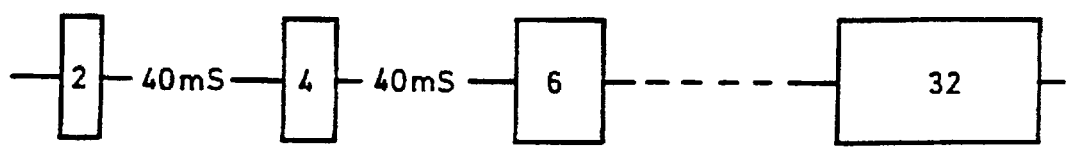
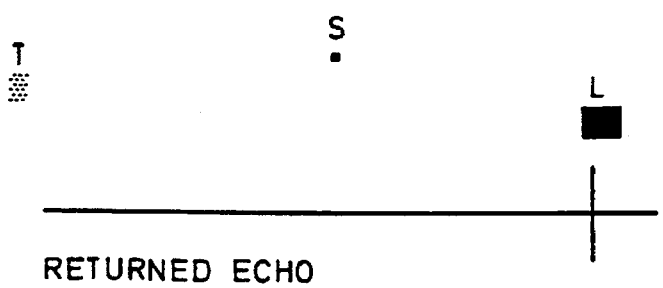
FIG. 5
RETURNED ECHO
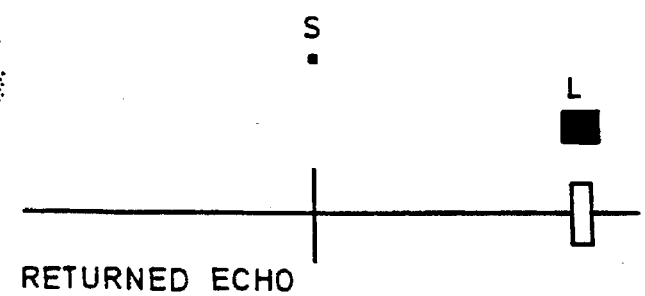
FIG. 6
RETURNED ECHO
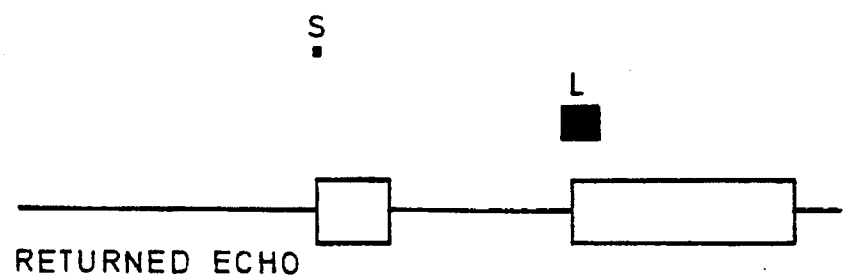
FIG. 7
RETURNED ECHO

FIG. 8

```
; clock = 16 MHz      tranducer = 40 KHz      pulse length = 96 cycles   "
; max resolution = 0.010mm      resolution = 0.176mm   sample rate = 24.9/s   "
" 8032 external data pg12 bitfg = 0  disfg = 0  items = 03  loc = NDAT-0   "
" !Quit!Pick!Man!Zerobuff!Run!Stop!daTaview!View!Nodis!Xramview!bit!   "
" ADD:  0  1  2  3  4  5  6  7  8  9  A  B  C  D  E  F   "
" 0000: 00 00 00 00 00 00 00 00 00 00 00 00 00 00 00 00   "
" 0010: 00 00 00 00 00 00 00 00 00 00 00 00 00 00 00 00   "
" 0020: 00 00 00 00 00 00 00 00 00 00 0C 0F 13 17 1B 20 24   "
" 0030: 00 0A 0A 0A 08 09 0A 0C 0F 13 17 1B 20 24   "
" 0040: 28 2C 2E 31 32 33 34 34 34 33 33 33 32 32 31   "
" 0050: 31 31 32 32 30 30 2F 29 1D 0E 00 BE BC C0 C4   "
" 0060: C7 02 09 0D 10 14 17 13 0B 07 04 01 C5 C3 C2 C2   "
" 0070: C1 C2 C2 C2 C7 C8 C1 C1 C1 C1 C1 C1 C2 C2 C3   "
" 0080: C4 C5 C5 C6 C7 C7 C8 C8 00 01 02 03 03 03 02 01   "
" 0090: 00 C7 C6 C5 C4 C4 C5 C6 C8 00 02 04 06 07 09   "
" 00A0: 0C 0D 0F 13 18 1F 26 2B 2F 31 33 34 35 36 37   "
" 00B0: 37 38 38 37 36 34 33 31 30 2F 2E 2D 2D 2D 2D   "
" 00C0: 00 00 00 00 00 00 00 00 00 00 00 00 00 00 00 00   "
" 00D0: 00 00 00 00 00 00 00 00 00 00 00 00 00 00 00 00   "
" 00E0: 00 00 00 00 00 00 00 00 00 00 00 00 00 00 00 00   "
" 00F0: 00 00 00 00 00 00 00 00 00 00 00 00 00 00 00 00   "
```

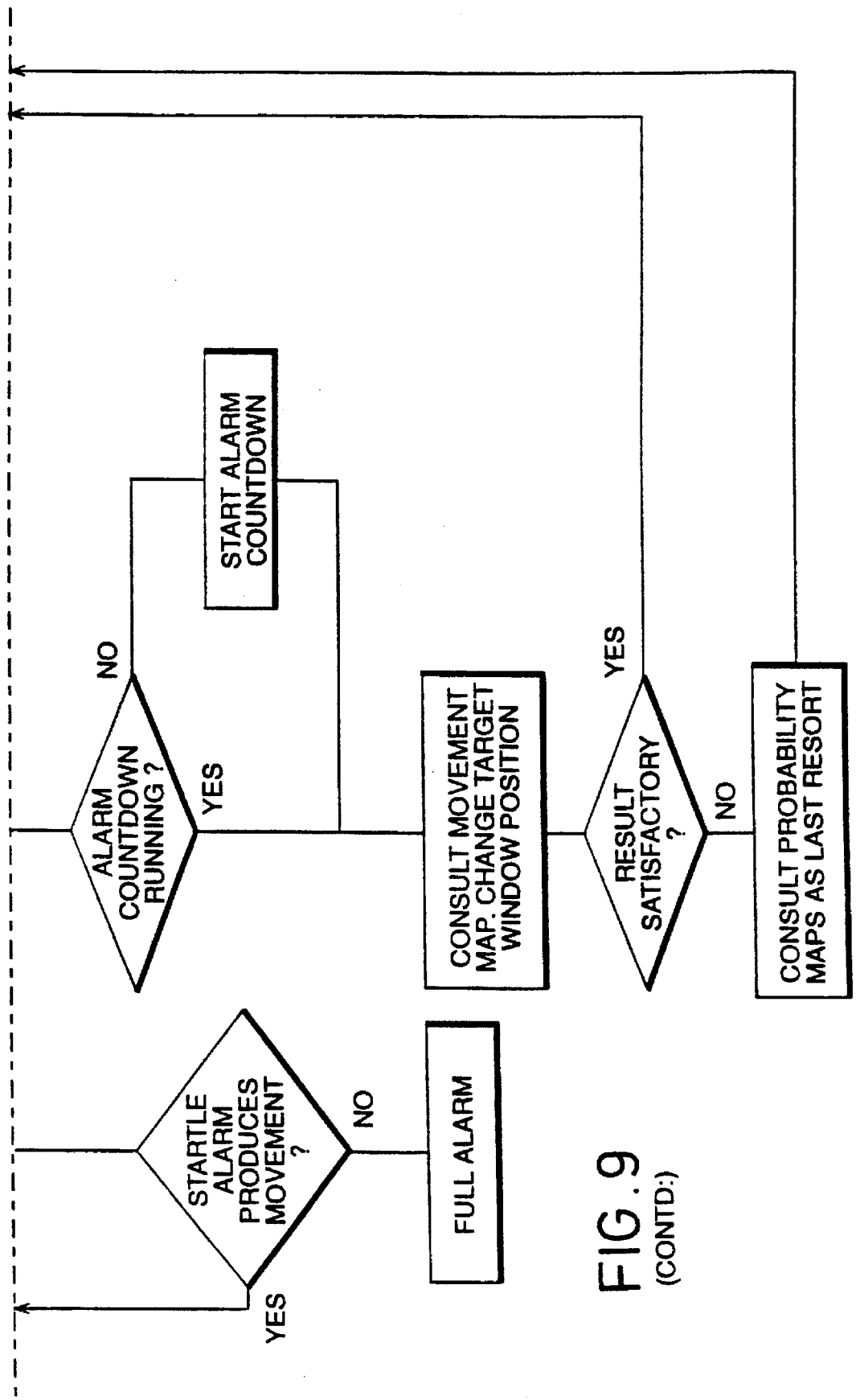
FIG. 9 (CONTD:)

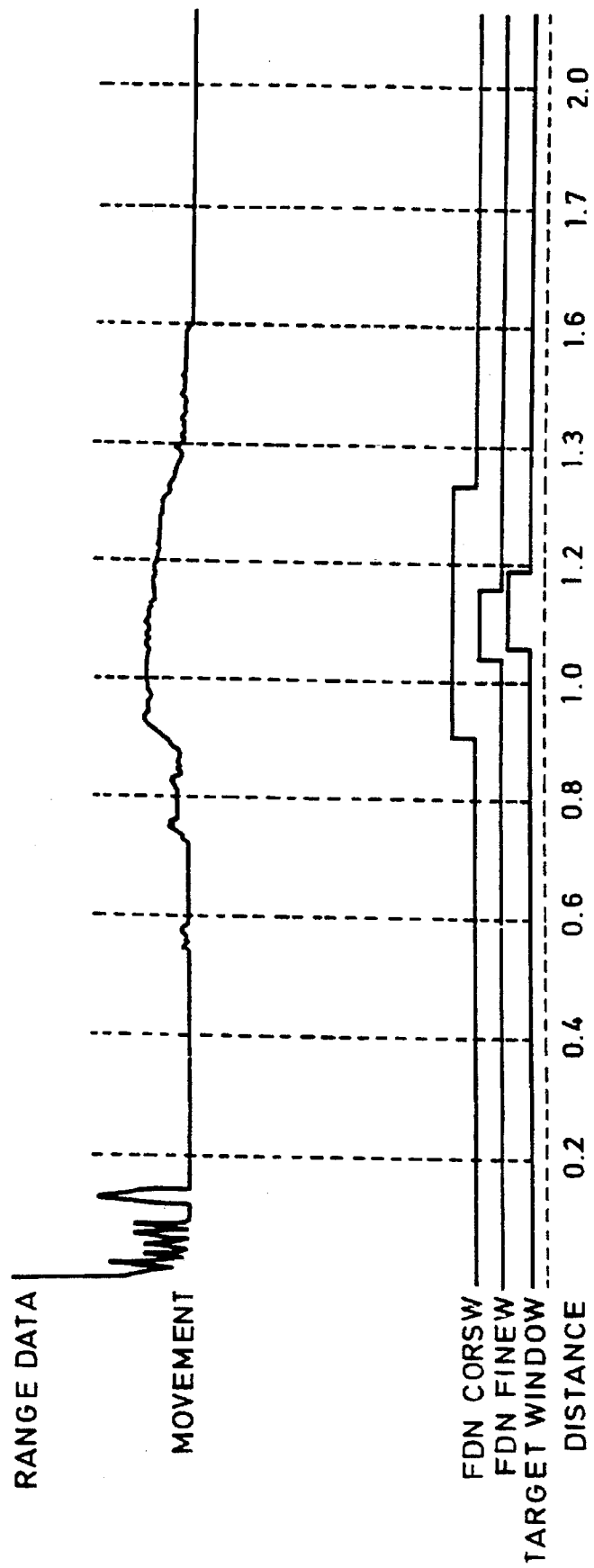

ULTRASONIC MONITOR

This invention relates to ultrasonic monitors. The invention is primarily concerned with ultrasonic movement monitors such as a monitor for monitoring breathing movement of a subject, which may be a human or other animal. However, the invention also relates to the measurement of the properties of fluids with ultrasonics, such as fluid viscosity measurement.

It has been proposed to monitor the breathing of a baby by monitoring ultrasonic waves reflected from the baby, in order to detect apnoea, the cessation of respiration. An alarm signal is initiated when breathing has ceased, to call the parent, or nurse in a hospital, so that urgent attention can be given.

In systems such as those proposed in Specifications Nos GB 2 192 713 and U.S. Pat. No. 4 197 856, a continuous ultrasonic wave is employed, and a phase-locked-loop is provided whereby the frequency of the ultrasonic source is varied. The analogue output signal of the phase-locked-loop represents the movement of the object in the time domain.

The known systems tend to produce false alarm signals because they can respond to movements of nearby objects, such as a person walking past a baby's cot. Attempts to render the existing systems more discriminating can lead to a loss in sensitivity to the baby's breathing.

According to a first aspect of the invention a movement monitor for monitoring the movement of an object comprises an ultrasound emitter and an ultrasound receiver adapted to receive sound waves reflected from the object, pulse energisation means for causing the emitter periodically to emit a burst of ultrasound pulses, and detection means responsive to the receiver to monitor the output of the receiver and to indicate an abnormal movement or lack of movement.

When the movement to be monitored is a cyclic movement the time period between successive bursts of ultrasound is arranged to be substantially less than the cycle time.

In addition to indicating abnormal movement or lack of movement, the detection means may be arranged to indicate normal movement.

Although the invention has been developed for use as a movement monitor, we consider that there would be advantages in applying digital phase discrimination analysis techniques to the measurement of properties of fluids. We have realised that if an ultrasonic wave is transmitted through a fluid from an emitter to a receiver, and the condition of the fluid changes in some way, the change can result in a phase shift in the received signal.

According to a second aspect of the invention an ultrasonic monitor comprises an ultrasound emitter and an ultrasound receiver, a fluid chamber interposed in the sound path between the emitter and receiver whereby ultrasound passes through the fluid in the chamber, digital phase monitoring means responsive to the input to the emitter and to the output from the receiver and adapted to monitor the changes in the phase relationship between said input and said output.

Such a monitor may be used, for example, to monitor changes in the fluid in said chamber, such as temperature change, which will alter the sound velocity and consequently alter the phase relationship between said input and said output. Viscosity or composition changes in the fluid too may be associated with changes in sound velocity, and thus be measurable.

Such a monitor may, for example, be used to measure the velocity of a fluid by arranging for the ultrasound to be transmitted parallel to the direction of fluid travel in the chamber, thereby to alter the effective ultrasound velocity through the chamber. Since fluid velocity can be a measure of the viscosity of a fluid, for a given applied pressure difference to the fluid, the phase changes between said input and said output may also be arranged to be a measure of viscosity change.

An ultrasonic monitor in accordance with the second aspect of the invention may incorporate a fixed ultrasound reflector whereby the waves pass in two directions through the fluid from the emitter to the receiver, which can then be positioned adjacent to the emitter.

In a preferred arrangement of a monitor in accordance with the first or the second aspect of the invention, the ultrasound emitter has periods of inactivity so as to overcome the problem of crosstalk with the ultrasound receiver.

Preferably the ultrasound pulses are emitted at an optimum frequency for the emitter.

Except for use in fluid velocity measurement, the ultrasound emitter means and the ultrasound receiver means are preferably mounted close to each other, most preferably together, in one unit, and in a further preferred arrangement, the ultrasound emitter and receiver together comprise a single transducer element which is adapted for switching between emitter function and receiver function.

The detection means may desirably be arranged to compare the output of the receiver with previous outputs, and to provide an alert output when the receiver output, or a component thereof, remains substantially unchanged for more than a predetermined period.

When the monitor is used as a breathing monitor, the alert output is preferably arranged to initiate a startle routine in which the monitored subject is exposed to a startle stimulus, such as a loud noise, and the response of the subject to the stimulus is detected by the detection means.

Such an arrangement is particularly suitable for monitoring a baby, but it may be used with an elderly patient.

Preferably it is arranged that an alarm signal is initiated after a failure to startle the subject into breathing.

It is recognised that the size and weight of a new born baby is very much different to that of a child of some 18 months old and that the pattern and depth of movement both from breathing and other activities is markedly different. Preferably, therefore, a baby movement monitor comprises controlling software or firmware arranged automatically to adapt the movement monitor detection parameters to suit developmental changes in an infant such that a single movement monitor can be used throughout the vulnerable period of development of the infant.

An important feature of the invention is in the realisation that there will be a substantially fixed phase relationship between the on-going transmitter drive oscillations, still continuing within the device although expressed only intermittently at the output amplifier, and returned signal oscillations ere these are reflected from fixed objects, and that there will be a varying phase difference between these two signals and returned signal oscillations reflected from moving objects, and that furthermore the varying magnitude of this phase difference will bear a substantially linear relationship to the magnitude of the movement and the rate of change of phase difference will represent the velocity of this movement thus enabling measurement of both the distance moved by objects and their velocity. Preferably phase difference detection is provided by fully digital means so as to prevent errors that can arise in processing analogue signals from phase detectors. Preferably the movement monitor is adapted to derive timing and counting pulses from a single master system clock so as to synchronise the processing device clock and instruction execution, the phase detector clock and the ultrasonic drive oscillator in order to overcome errors introduced by timing jitter.

The resolution of the movement detection system and the accuracy with which movement can be detected are functions of the stability of the phase detector and the frequency of the phase detector clock. The bandwidth and range of the system are limited by the repetition frequency and duration of the burst of ultrasound pulses.

Preferably the master clock is adapted to run at high frequency, most preferably in the range 10 to 30 MHz.

A preferable feature of the invention is concerned with the training of the detection means to discriminate between ultrasonic reflections from an object to be monitored, and reflections from other objects, such as stationary cot bars, and is based upon the principles described above.

In accordance with the preferable feature, the detection means is arranged to identify particular objects in the field of view of the receiver by analysing the sequence of phase difference signals pulse by pulse and identifying correlated relationships within groups, and to memorise characteristics of the echo signal, and during subsequent monitoring to discriminate between various echo signals, whereby an alarm signal is generated only in response to an undesirable condition in a particular selected object.

The training sequence preferably comprises causing the emitter to emit 'bursts' of ultrasound pulses, the bursts having different durations, and monitoring the durations of the resulting echoes received from different objects, the change in duration of an identifiable echo corresponding to a particular object with the change in duration of the emitter pulse being monitored, in order to establish a memory profile of that object, memory profiles being established in this way for each of the objects in the field of view of the receiver that receive ultrasonic emissions.

Then, in normal operation of the monitor, the echoes from objects other than the particular object to be monitored are disregarded, and an alarm signal is generated only in response to an abnormal condition being detected in the movement or lack of movement of the particular object.

According to a third aspect of the invention we provide an ultrasonic monitor for monitoring the movement of an object comprising an ultrasound emitter, an ultrasound receiver adapted to receive sound waves reflected from the object, pulse energisation means for causing the emitter periodically to emit a burst of ultrasound pulses, and detection means responsive to the receiver to monitor the output of the receiver, the detection means being arranged to identify particular objects in the field of view of the receiver by analysing the sequence of phase difference signals pulse by pulse and by identifying correlated relationships within groups of pulses, and to memorise characteristics of the echo signal, and during subsequent monitoring to discriminate between various echo signals, whereby an indication signal indicative of the condition of an object is generated by the detection means only in response to the condition of a particular selected object.

According to a fourth aspect of the invention we provide an ultrasonic monitor for monitoring the movement of an object comprising an ultrasound emitter, an ultrasound receiver adapted to receive sound waves reflected from the object, pulse energisation means for causing the emitter periodically to emit a burst of ultrasound pulses, and detection means responsive to the receiver to monitor the output of the receiver, the monitor having a training sequence which comprises causing the emitter to emit 'bursts' of ultrasound pulses, the bursts having different durations, and monitoring the durations of the resulting echoes received from different objects, the change in duration of an identifiable echo corresponding to a particular object with the change in duration of the emitter pulse being monitored, in order to establish a memory profile of that object, memory profiles being established in this way for each of the objects in the field of view of the receiver that receive ultrasonic emissions.

A further implementation of a movement monitor in accordance with the invention is for low frequency vibration monitoring of civil engineering structures such as bridges, buildings, chimneys etc. In this application the required bandwidth would be from 1/10th Hz to 10 Hz with resolution down to less than 0.1 mm.

A baby breathing monitoring apparatus in accordance with the invention will now be described, by way of example only, with reference to the accompanying drawings, in which:

FIGS. 4 to 7 are diagrams to show the principles behind the training sequence;

FIG. 8 represents a series of one-dimensional arrays of data recorded in the normal operating mode;

FIG. 10 is a graphical representation of echo signal data.

HARDWARE

Figure 1:
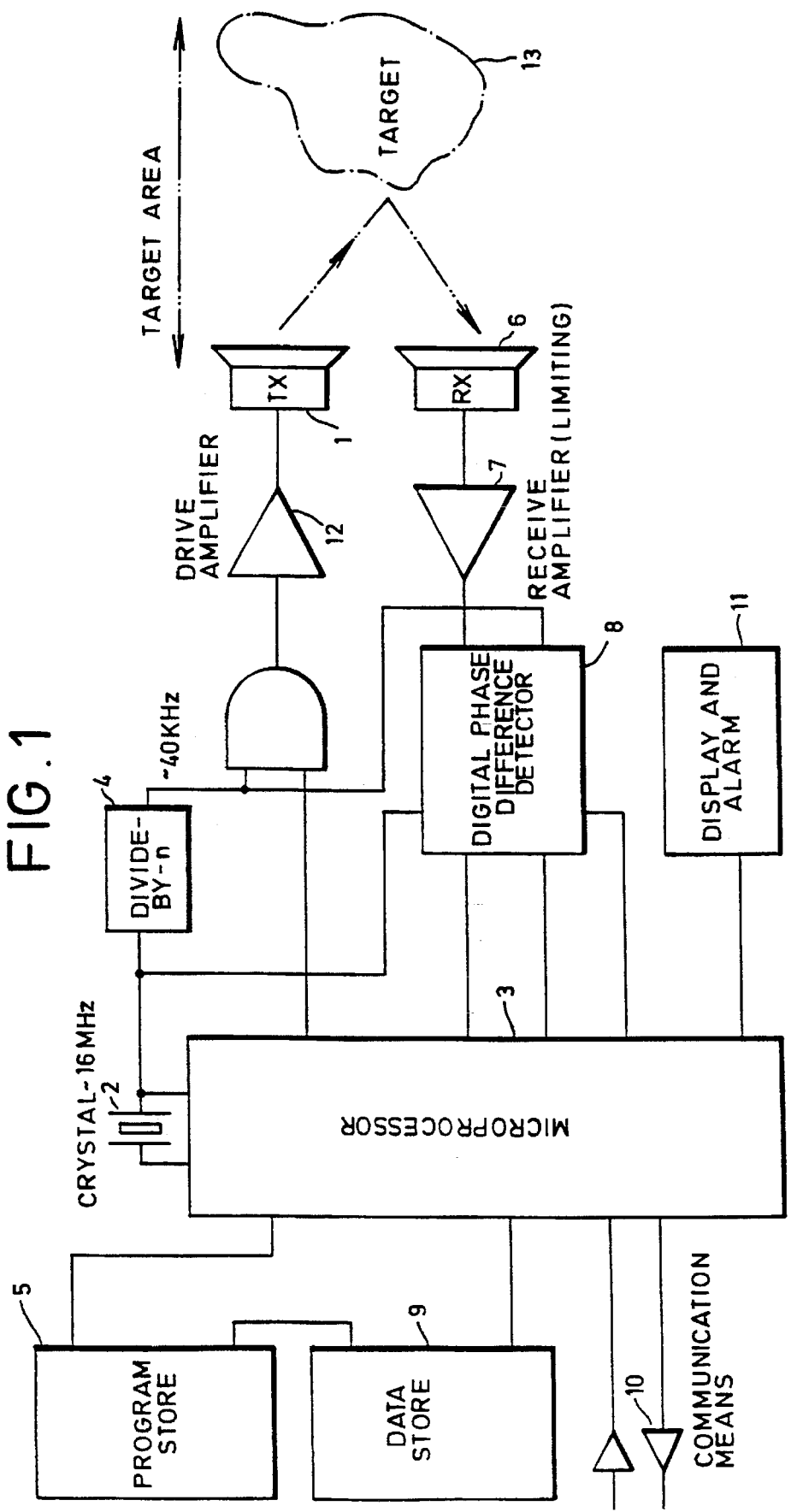
FIG. 1 is a block circuit diagram of the apparatus.

With reference to FIG. 1, an ultrasonic transmitter transducer 1 is driven by amplifier 12 at a fixed frequency from frequency divider 4 which is a precise division of the main microprocessor crystal controlled oscillator or clock 2. In the normal monitoring mode, a burst of oscillations is transmitted periodically, the duration of which is controlled by the microprocessor 3 and its sequencing software stored in the program memory 5. The ultrasonic echo returned from the target area is sensed by the ultrasonic receiver 6 and the resulting signal is processed by amplifier 7 with sufficient gain to produce limiting on normally expected echo amplitude signals. This signal is fed to the digital phase difference detector 8 which is under the control of the microprocessor 3 and which produces a digital output for each oscillation of the returned echo signal. The high frequency processor clock is used as the clock to drive the phase difference counter within the phase difference discriminator. The microprocessor reads these numbers and enters them into the data store 9 for processing under control of the analysis software also stored in the program memory 5.

The system is implemented utilising standard HCMOS logic elements.

Communicating means 10 is provided for connection to a computer or network to produce detailed analysis of the movement detection whereas display and alarm means 11 are provided for local indication.

The design of the logic permits only one element of the transmitter or receiver transducer to be active at any one time.

Figure 2:
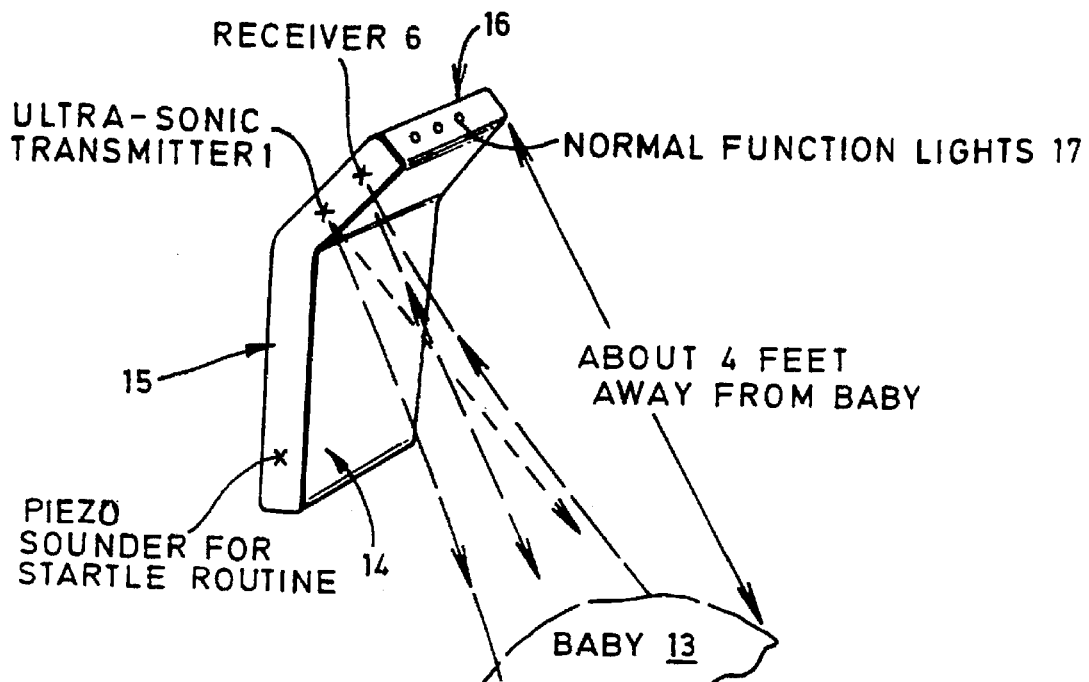
FIG. 2 is a perspective view of the apparatus shown in its position of use.

As shown in FIG. 2, the apparatus comprises a housing 14 having an upright limb 15 and an overhanging limb 16 extending at an obtuse angle with respect to the upright limb 15, the transmitter 1 and receiver 6 being housed within the limb 16 such that the conical fields of emission and reception are directed generally downwards whereby when the limb 15 is secured to the side of a cot, or to a wall alongside a cot, the conical fields point at the central region of the floor of the cot.

SOFTWARE

Figure 9:
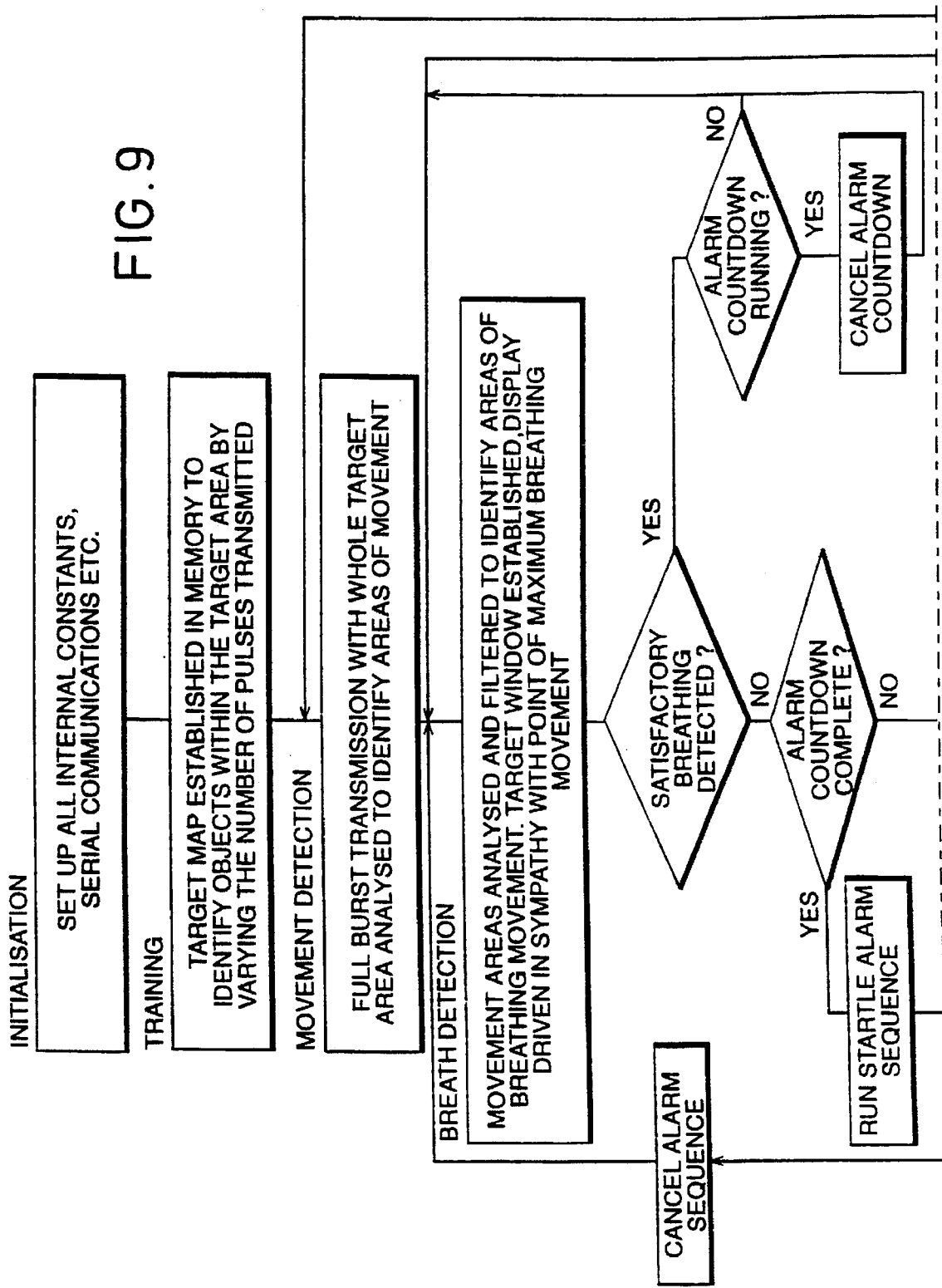
FIG. 9 is a flow chart showing the software function.

The main sequences performed by the software are shown in FIG. 9. Initially, by software control, a training mode is initiated. This mode is described in more detail hereafter. Essentially, a short burst of pulses is transmitted. The returned signal is then processed to determine where the target object lies. Software then uses this information to determine the active zone in which it must scan. This training mode is maintained until a steady 'target zone' has been established.

At this point, the software changes to a normal operating mode for movement and breath detection, and initiates regular pulse bursts of longer duration. The returned pulses and time differences between adjacent pulses are then analysed. This information is stored and used to create a software profile or movement map representative of regular breathing. A 'startle' sequence is initialised when the breathing is too shallow for too long, when the period between detected breaths is too long, or when there is an absence of breathing after breathing has been detected. This latter case will initiate an alarm sequence. If, after a startle stimulus, a response is detected, but no breath can be detected after that, then the startle will sound again, and if the same applies again after that then a pulsed alarm is sounded which indicates potential trauma.

The unit is preferably capable of emitting startle or alarm sounds at various manually adjustable levels, frequencies and durations.

The software is adaptive to the extent that in the training mode ranging to detect the target zone is automatic, providing that the target is typically within 2–6 feet of the unit and, similarly, creation of the breathing profile is automatic.

TRAINING MODE

Figure 3:
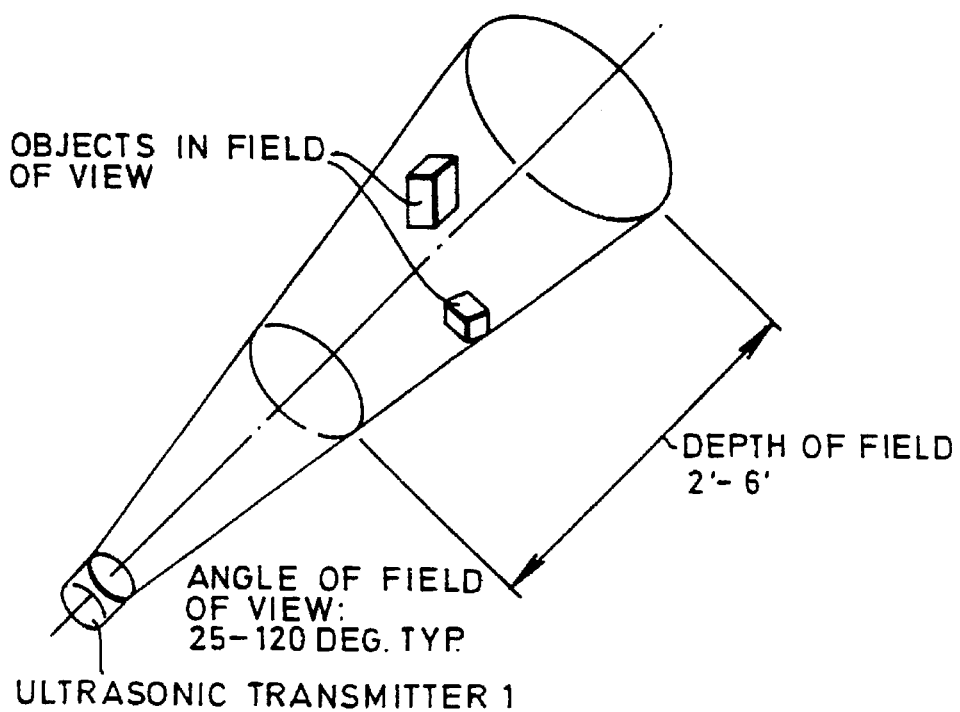
FIG. 3 shows the conical field of view of the receiver.

When the unit commences operation, it is essential to know where, within the field of view, the target object lies. In practice, this field of view is conical in shape, as in FIG. 3, with the apex of the cone being the ultrasonic transducer transmitter. The angle of divergence of the cone is arbitrary and is determined only by the characteristic of the particular type of transducer being used. In practice, this angle may lie typically within 25°–120°. The depth of field may be as much as 6 feet, although in practice best results have been obtained when target objects are within 2–6 feet of the transmitter. Any object or objects within this field will, when struck by an ultrasonic wave, return an echo to the ultrasonic transducer receiver 6. The magnitude of the returned echo is related to the size of the object.

In order to establish what object or objects lie in the field of view, the microprocessor software initiates a sequence whereby 16 'bursts' of ultrasound are transmitted. The first burst comprises exactly 2 ultrasonic cycles, the second burst exactly 4 cycles, the third exactly 6 cycles and so on, until the 16th burst which comprises 32 cycles. This is indicated in FIG. 4. After each burst, a delay of 40 mS is introduced, thereby providing means of discrimination between adjacent bursts.

With reference to FIG. 5, consider the effect of these bursts of ultrasound when directed into the field of view. Although shown there as a 2-dimensional representation, in reality any object in the 3-dimensional field covered will return an ultrasonic echo.

After transmitter T has completed sending the first burst of 2 cycles, small object S will, because of its small size, return little or no echo. The larger object L will, because of its greater size, return a larger signal. This returned echo is shown on the left.

After the transmitter T has completed sending the second burst of 4 cycles, any returned echo from either of the objects will be proportionately larger, as shown in FIG. 6.

Similarly, as the transmitted burst becomes progressively longer, so the returned echo will also become longer, dependant on the size of the object, as shown in FIG. 7.

It should be noted that it is quite possible, yet permissible, for echoes to overlap. That is to say, that if object S were in close proximity to object L, then after a long burst of ultrasound the trailing edge of the echo from S may overlap with the leading edge of the echo from L. The software data compression technique used initially would still allow a distinction to be made between the two objects.

The microprocessor and hardware capture the returned signal echo after each of the 16 transmitted bursts. It should be noted that amplitude of the signal is unimportant; only the duration of the returned echo in each case. This duration is measured in terms of a number of microprocessor clock oscillator periods. Since this oscillator is a stable crystal controlled device running typically at more than 10 MHz, then timing period accuracy of 100 nS or better may be achieved.

The captured data, after each transmitted burst, undergoes data compression and the resulting 16 bytes of data are stored sequentially in memory. Essentially, after data compression, the presence of an echo is stored in memory as FF hexadecimal, and no echo stored as 00. The following table shows this pictorially:

TABLE

| Data after burst: | |
|---|---|
| 1: | 00 00 00 00 00 00 00 00 FF 00 00 00 00 00 00 00 |
| 2: | 00 00 00 FF 00 00 00 00 FF FF FF 00 00 00 00 00 |
| 3: | 00 00 00 FF FF 00 00 00 FF FF FF FF 00 00 00 00 |
| . | |
| . | |
| 15: | 00 00 00 FF FF FF FF 00 FF FF FF FF FF FF FF FF |
| 16: | 00 00 00 FF FF FF FF FF FF FF FF FF FF FF FF FF |

The number of FF and zero values appearing in each column is then totalised; a high numeric total indicating a large object and its physical position and a lower number indicating a smaller object and its physical position. For each object located, a dedicated table of data is created in the microprocessor's memory in order to evaluate echo data returned from each object. Each table may be said to represent a window on to a particular area within the field of view.

Once the approximate positions of target objects have been evaluated and a data window created for each, the software enters a loop whereby a similar sequence of ultrasonic bursts are transmitted, but each burst is of rather longer duration than that used by the initial ranging sequence. Returned data undergoes data compression as before, but to a lesser extent. This yields a greater amount of data (or at least data of higher resolution) to be stored in each window. After a number of program loops, it is possible to determine which windows contain data from static objects, eg the rails of a child's cot, and which windows contain data derived from dynamic targets, e.g. a moving infant. For a baby monitor, the microprocessor's software discards information returned by static objects.

Once the active window(s) has been selected, data is continuously analysed until a regular breathing pattern emerges. The software has now completed its training or auto-ranging phase and exits to the normal monitoring phase.

NORMAL OPERATING MODE

In normal operation, the software analyses the profile of movement within the target area and discriminates between random movements which may be caused typically by air currents or by cot blankets settling and regular repetitive movements characteristic of a child breathing whilst asleep. The point at which maximum depth of breathing movement is detected is then classified as the centre of the target and a window of a burst of 16 contiguous ultrasonic oscillations centred on this distance is analysed in considerable detail. This is defined as the target window.

FIG. 8 represents a series of one dimensional 16 bit arrays which record the oscillations reflected from the window. The array is recorded in time with a base frequency of, for example, 20 Hz, which is typically one half of the frequency of the emitted burst.

A series of zeros at the beginning or end of an array shows a period during which no output was taken from the receiver. Other numbers in the array having values from 00 to a maximum of C6 are representative of the magnitude of the phase difference between the base and each signal received as an echo of one pulse from the emitted burst, ranging from nothing to the maximum phase difference (180°).

Where a sequence of similar numbers appears, for example as in line 0070 of FIG. 8, the sequence is likely to represent a fragment of the emitted burst reflected from some object in the window, the position of the sequence in the array corresponding to the distance of the object from the transmitter.

By comparing the change between sequences in the arrays recorded for successive bursts, the software is able to identify an object having a regular movement of, say 15–62 cycles per minute, indicative of a baby breathing. When such movement ceases, or insufficient movement is detected, the startle sequence is initialised, as outlined above.

If the baby changes its position in the cot so much so that the maximum amount of movement is no longer near the centre of the target window, then the position of the target window is adjusted in order to track the new position of the baby.

If the baby is awake and continuously wriggling or moving about the cot then breathing patterns can no longer be sensed accurately. This is not important as such movement is taken as an indication of the continuing well-being of the baby.

A significant factor in the success and acceptability of an apnoea monitor is in its ability not to produce false alarms and much of the software running at less regular intervals is involved in ensuring that the target window tracks the movement of the baby.

For example, six times a second a ranging routine is executed which checks the input data for target identification using the predefined rules and adjusts the target window if necessary.

Once every four seconds another routine analyses the movement profile in the whole target area to identify where recognisable breathing movements are taking place.

A number of probability images are constructed which log events and their positions in the target window.

In the event of breathing movement ceasing, the alarm countdown of 15 seconds begins and the software commences an intelligent scan of the data bank which it has constructed in order to try to recognise breathing movement and prevent a false alarm.

Firstly, the good target position is checked, then the position of filtered output peaks then the position of movement peaks and finally the probability maps of previous events. If no movement is detected then the alarm sequence is initiated at the end of the countdown period.

Lights 17 on the housing 14 can be arranged to indicate normal functioning of the apparatus. Preferably the lights are arranged in a row and whilst regular breathing movement is being detected, are lit sequentially from one end so as to form an illuminated "bar graph" which varies in sympathy with this movement indicating the breathing pattern. Any irregular movements such as the baby turning over or waving an arm in the air will be detected and may cause brief irregular changes to the display pattern but the software continues to monitor in the target window.

FIG. 10 shows a graphical representation plotted on a computer screen of some of the parameters extracted from the echo signals by the microprocessor software, the x-axis giving the distance from the monitor in meters. The top trace shows amplitude of movements occurring within the field of view, the most pronounced movements in this example being shown by the hump between about 0.8M and 1.3M. The next trace shows the distance over which phase differences between successive arrays are less than $5/198$ of one wavelength, and the next trace the distance over which the phase differences are less than $2/198$ of one wavelength. The bottom trace identifies a window, containing 16 consecutive locations spaced 8.3 mm apart in the direction of the x-axis, in which the most pronounced regular movement is occurring.

Where the monitored object undergoes a cyclic movement the detection means of the monitor may be used to provide a signal indicative of the phase of the movement. Thus a signal could be generated at a predetermined phase of each cycle of movement, and this predetermined phase could be made adjustable. This signal may be used to trigger an associated apparatus.

Although the apparatus described has been described with reference to the monitoring of the breathing of a baby, modified apparatus could be used to monitor heart beat. Indeed, the apparatus could be used for monitoring the movement of objects, in industrial process control, for example.

With a breathing monitor it is necessary to filter out the signals due to movement of the chest caused by heart beat, but when it is desired to monitor heart beat, it is of course necessary to filter out the component due to breathing. If desired, both heart beat and breathing components could be monitored.

I claim:

1. An ultrasonic monitor for monitoring the movement of an object (13) comprising an ultrasound emitter (1), an ultrasound receiver (6) adapted to receive sound waves reflected from the object (13), pulse energisation means (12) for causing the emitter periodically to emit a burst of ultrasound pulses, and detection means (8) responsive to the receiver to monitor the output of the receiver and to indicate an abnormal movement, relative to specified parameters for normal movement of the object, or a lack of movement, characterised in that the detection means comprises digital phase monitoring means (8) responsive to the input to the emitter and to the output from the receiver and adapted to monitor the changes in the phase relationship between said input and said output.

2. An ultrasonic monitor as claimed in claim 1 characterised in that the detection means is arranged also to indicate normal movement.

3. An ultrasonic monitor as claimed in claim 2 characterised by lights (17) which are arranged to be lit sequentially in sympathy with the cyclic movement of an object executing a cycle of movement.

4. An ultrasonic monitor as claimed in any of the preceding claims characterised in that the detection means (8) is arranged to compare the output of the receiver (6) with previous outputs of the receiver, and to provide an alert output when the receiver output, or a component thereof, remains substantially unchanged for more than a predetermined period.

5. An ultrasonic monitor as claimed in claim 4 characterised in that the monitor is adapted for use as a baby breathing monitor, the monitor being capable of detecting breathing movement of a baby, and comprising a startle producing means, responsive to the alert output to initiate a startle routine in which the monitored subject (13) is exposed to a startle stimulus, and the response of the subject to the stimulus is detected by the detection means (8).

6. An ultrasonic monitor as claimed in claim 5 characterised in that an alarm signal is initiated after a failure to detect breathing movement of the baby (13) following the production of a startle stimulus by said startle producing means.

7. An ultrasonic monitor as claimed in claim 5 characterised by controlling software or firmware which is arranged automatically to adapt the monitor detection parameters to suit developmental changes in an infant such that the monitor can be used throughout the vulnerable period of development of the infant.

8. An ultrasonic monitor as claimed in any one of claims 1 to 3 characterised in that the detection means (8) is arranged to identify particular objects in the field of view of the receiver (6) by analysing the sequence of phase difference signals pulse by pulse and by identifying correlated relationships within groups of pulses, and to memorise characteristics of the echo signal, and during subsequent monitoring to discriminate between various echo signal, whereby an indication signal indicative of an abnormal movement or lack of movement is generated only in response to the condition of a particular selected object (13).

9. An ultrasonic monitor as claimed in any one of claims 1 to 3 characterised in that the monitor has a training sequence which comprises causing the emitter (1) to emit 'bursts' of ultrasound pulses, the bursts having different durations, and monitoring the durations of the resulting echoes received from different objects, the change in duration of an identifiable echo corresponding to a particular object (13) with the change in duration of the emitter pulse being monitored, in order to establish a memory profile of that object, memory profiles being established in this way for each of the objects in the field of view of the receiver that receive ultrasonic emissions.

10. An ultrasonic monitor as claimed in claim 9 characterised in that the monitor has a normal operation following the training sequence in which the echoes from objects other than the particular object (13) to be monitored are disregarded, and an alarm signal is generated only in response to an abnormal condition being detected in the movement or lack of movement of the particular object (13).

11. An ultrasonic monitor as claimed in claim 1 or claim 2 characterised in that the monitor is adapted for low frequency vibration monitoring of civil engineering structures by having a bandwidth substantially in the range 1/10 th Hz to 10 Hz with resolution down to less than 0.1 mm.

12. An ultrasonic monitor for monitoring the movement of an object (13) comprising an ultrasound emitter (1), an ultrasound receiver (6) adapted to receive sound waves reflected from the object (13), pulse energisation means (12) for causing the emitter periodically to emit a burst of ultrasound pulses, and detection means (8) responsive to the receiver to monitor the output of the receiver, the detection means (8) being arranged to identify particular objects in the field of view of the receiver (6) by analysing the sequence of phase difference signals pulse by pulse and by identifying correlated relationships within groups of pulses, and to memorise characteristics of the echo signal, and during subsequent monitoring to discriminate between various echo signals, whereby an indication signal indicative of the condition of an object is generated by the detection means only in response to the condition of a particular selected object (13).

13. An ultrasonic monitor for monitoring the movement of an object (13) comprising an ultrasound emitter (1), an ultrasound receiver (6) adapted to receive sound waves reflected from the object (13), pulse energisation means (12) for causing the emitter periodically to emit a burst of ultrasound pulses, and detection means (8) responsive to the receiver to monitor the output of the receiver, the monitor having a training sequence which comprises causing the emitter (1) to emit 'bursts' of ultrasound pulses, the bursts having different durations, and monitoring the durations of the resulting echoes received from different objects, the change in duration of an identifiable echo corresponding to a particular object (13) with the change in duration of the emitter pulse being monitored, in order to establish a memory profile of that object, memory profiles being established in this way for each of the objects in the field of view of the receiver that receives ultrasonic emissions.

14. An ultrasonic monitor as claimed in any of claims 1 to 3, 12 or 13 in which the detection means is adapted for monitoring the movement of a cyclically movable object, the detection means being so arranged as to provide a signal at a predetermined phase of the cycle of movement of the object.

15. An ultrasonic monitor as claimed in claim 14 comprising means for adjusting the phase at which said signal is generated.

16. An ultrasonic monitor for monitoring changes in a fluid comprising an ultrasound emitter (1) and an ultrasound receiver (6), a fluid chamber being interposed in the sound path between the emitter (1) and receiver (6) whereby ultrasound passes through the fluid in the chamber, and digital phase monitoring means (8) responsive to the input to the emitter and to the output from the receiver and adapted to monitor the changes in the phase relationship between said input and said output.

17. An ultrasonic monitor as claimed in claim 16 characterised by a fixed ultrasound reflector whereby the waves pass in two directions through the fluid from the emitter (1) to the receiver (6).

18. An ultrasonic monitor as claimed in any one of claims 1 to 3, 12, 13, 16 or 17 characterised in that the ultrasound emitter (1) and the ultrasound receiver (6) are mounted close to each other.

19. An ultrasonic monitor as claimed in claim 18 characterised in that the ultrasound emitter (1) and the ultrasound receiver (6) are mounted together in one unit.

20. An ultrasonic monitor as claimed in any one of claims 1 to 3, 12, 13, 16 or 17 characterised in that the ultrasound emitter (1) and receiver (6) together comprise a single transducer element which is adapted for switching between emitter function and receiver function.

21. An ultrasonic monitor as claimed in claim 16 or 17 characterised in that the monitor is adapted for monitoring changes in the velocity of the fluid.

22. An ultrasonic monitor as claimed in claim 16 or 17 characterised in that the monitor is adapted for monitoring changes in the viscosity of the fluid.

23. An ultrasonic monitor as claimed in any one of claims 1 to 3, 12, 13, 16 or 17 characterised in that the ultrasound emitter (1) has periods of inactivity so as to overcome the problem of crosstalk with the ultrasound receiver (6).

24. An ultrasonic monitor as claimed in any of claims 1 to 3, 12, 13, 16 or 17 characterised in that the monitor is adapted to derive timing and counting pulses from a single master system clock (2) so as to synchronise the processing device clock and instruction execution, the phase detector clock and the ultrasonic drive oscillator in order to overcome errors introduced by timing jitter.

25. An ultrasound monitor as claimed in claim 24 characterised in that the master clock is adapted to run at a high a frequency substantially in the range 10 to 50 MHz.

26. A method of monitoring changes in a fluid comprising transmitting ultrasound through the fluid from an ultrasound emitter (1) to an ultrasound receiver (6) by providing an input to the ultrasound emitter, deriving an output from the receiver, and using digital phase monitoring means (8) responsive to said input and said output to monitor changes in phase relationship between said input and said output.

27. A method as claimed in claim 26 characterised in that the velocity of flow of a fluid is monitored by arranging for the ultrasound to be transmitted parallel to the direction of flow, changes in said phase relationship being used to calculate changes in the velocity.

28. A method as claimed in claim 27 characterised in that the viscosity of a fluid is monitored by causing the fluid to flow parallel to a direction of transmission of the ultrasound from said ultrasound emitter to said ultrasound receiver, changes in said phase relationship being used to calculate a change in the viscosity of said fluid that occurs when the velocity of the flow of the fluid changes.

29. The invention claimed in any one of claims 1 to 3, 12, 13, 16, 17, 26, 27 or 28 characterised in that phase difference detection is provided by fully digital means.

* * * * *